United States Patent [19]

Winters et al.

[11] 4,232,017
[45] Nov. 4, 1980

[54] TREATMENT OF PSYCHIC DISORDERS AND INFLAMMATION WITH FUSED ISOQUINOLINES

[75] Inventors: Giorgio Winters; Nunzio Di Mola, both of Milan, Italy

[73] Assignee: Gruppo Lepetit S.p.A., Milan, Italy

[21] Appl. No.: 41,356

[22] Filed: May 22, 1979

[30] Foreign Application Priority Data

May 26, 1978 [GB] United Kingdom .............. 23106/78

[51] Int. Cl.³ ..................... A61K 31/54; A61K 31/47; C07D 471/04; C07D 513/04
[52] U.S. Cl. ............................. 424/246; 424/248.57; 424/250; 424/258; 544/58.6; 544/60; 544/176; 544/361; 546/82; 546/83
[58] Field of Search .................... 546/82, 83; 544/361, 544/126, 58, 60, 58.6; 424/246, 248.57, 250, 258, 248.51, 248.55

[56] References Cited

U.S. PATENT DOCUMENTS

| | | | |
|---|---|---|---|
| 3,630,745 | 12/1971 | Beavers et al. | 546/83 X |
| 3,816,429 | 6/1974 | Finch | 546/126 X |
| 3,890,324 | 6/1975 | Katner | 546/82 |
| 4,113,731 | 9/1978 | Winters et al. | 546/82 X |

OTHER PUBLICATIONS

March, J., *Advanced Organic Chemistry*, McGraw Hill, New York, 1968, pp. 298, 331 and 343.
Winters, G., et al., *Tett. Lett.*, #44, 3877-3878 (1975).

*Primary Examiner*—Henry R. Jiles
*Assistant Examiner*—Richard A. Schwartz

[57] ABSTRACT

New tricyclic ortho-fused heterocyclic compounds of formula

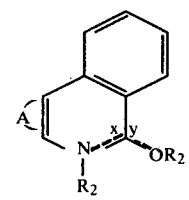

wherein A is the group

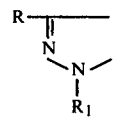

or the group

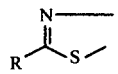

in which R represents hydrogen, $(C_{1-4})$alkyl, phenyl or tolyl and $R_1$ and may be $(C_{1-4})$alkyl, phenyl or tolyl, $R_2$ is selected from $(C_{1-4})$alkyl, $(C_{2-4})$alkanoylmethyl, carbo$(C_{1-3})$alkoxymethyl, hydroxy$(C_{2-4})$alkyl, halo$(C_{2-4})$alkyl and a group

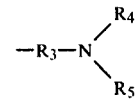

wherein $R_3$ is an alkylene group from 2 to 4 carbon atoms and $R_4$ and $R_5$ independently represent hydrogen or $(C_{1-4})$alkyl or, taken together with the nitrogen atom, a fully hydrogenated 5 or 6 membered heterocyclic radical which may contain a further heteroatom selected from O, N and S and be optionally substituted by a $(C_{1-4})$alkyl or phenyl group, or $R_2$ may represent, nil the dotted lines x and y may represent nil or additional bonds; with the proviso that, when the symbol $R_2$ linked to the oxygen atom is different from nil, x is an additional bond and y and the other symbol $R_2$ represent nil; with the further proviso that, when the symbol $R_2$ linked to the nitrogen atom is different from nil, y is an additional bond and x and the other symbol $R_2$ represent nil; and salts therewith of pharmaceutically acceptable acids. The compounds possess antiinflammatory, CNS-depressent and anti-anxiety utility.

9 Claims, No Drawings

TREATMENT OF PSYCHIC DISORDERS AND INFLAMMATION WITH FUSED ISOQUINOLINES

SUMMARY OF THE INVENTION

The present invention refers to new tricyclic ortho-fused heterocyclic compounds of formula

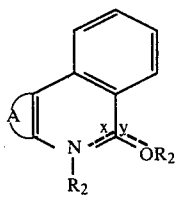

I wherein A is the group

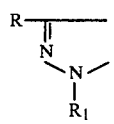

(a)

or the group

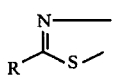

(b)

in which R represents hydrogen, $(C_{1-4})$alkyl, phenyl or tolyl and $R_1$ may be $(C_{1-4})$alkyl, phenyl or tolyl, $R_2$ is selected from $(C_{1-4})$alkyl, $(C_{2-4})$alkanoylmethyl, carbo$(C_{1-3})$alkoxymethyl, hydroxy$(C_{2-4})$alkyl, halo$(C_{2-4})$alkyl and a group

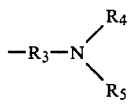

wherein $R_3$ is an alkylene group from 2 to 4 carbon atoms and $R_4$ and $R_5$ independently represent hydrogen or $(C_{1-4})$alkyl or, taken together with the nitrogen atom, a fully hydrogenated 5 or 6 membered heterocyclic radical which may contain a further heteroatom selected from O, N and S and be optionally substituted by a $(C_{1-4})$alkyl or phenyl group, or $R_2$ may represent nil, the dotted lines x and y may represent nil or additional bonds; with the proviso that, when the symbol $R_2$ linked to the oxygen atom is different from nil, x is an additional bond and y and the other symbol $R_2$ represent nil; with the further proviso that, when the symbol $R_2$ linked to the nitrogen atom is different from nil, y is an additional bond and x and the other symbol $R_2$ represent nil; and salts therewith of pharmaceutically acceptable acids. The compounds possess antiinflammatory, CNS-depressant and anti-anxiety utility.

When A represents the moiety (a), the compounds of formula I have the following structural formula

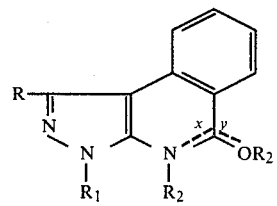

and are, therefore, pyrazolo[3,4-c]isoquinoline derivatives; when A represents the moiety (b), the compounds of formula I have the following structural formula

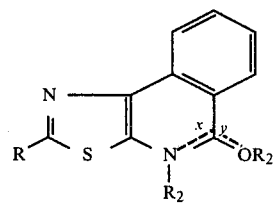

and are therefore, thiazolo[5,4-c]isoquinoline derivatives. The term "$(C_{1-4})$alkyl" as used herein identifies straight or branched alkyl radicals selected from methyl, ethyl, propyl, isopropyl, butyl, isobutyl, sec-butyl and tert-butyl. The alkylene groups essentially identify bis- or tris- or tetramethylene portions. The term "$(C_{2-4})$alkanoylmethyl" as used herein identifies radicals selected from acetylmethyl, propionylmethyl, butyrylmethyl, isobutyrylmethyl. The term "carbo$(C_{1-3})$alkoxymethyl" as used herein identifies radicals selected from carbomethoxymethyl, carbethoxymethyl or carbopropoxymethyl. The term "hydroxy$(C_{2-4})$alkyl" as used herein identifies straight or branched hydroxyalkyl radicals selected from 2-hydroxyethyl, 3-hydroxypropyl, 2-hydroxypropyl, 4-hydroxybutyl, 3-hydroxybutyl, 2-hydroxybutyl or 2-hydroxy-2-methylpropyl. The term "halo$(C_{2-4})$alkyl" as used herein identifies straight or branched haloalkyl radicals selected from 2-chloroethyl, 2-bromoethyl, 3-chloropropyl, 2-chloropropyl, 3-bromopropyl, 2-romopropyl, 4-bromobutyl, 4-chlorobutyl, 3-bromobutyl, 3-chlorobutyl, 2-bromobutyl, 2-chlorobutyl, 2-bromo-2-methylpropyl, 2-chloro-2-methylpropyl, 2-iodoethyl, 3-iodopropyl or 4-iodobutyl. Examples of the above mentioned heterocyclic radicals are pyrrolidinyl, piperidinyl, piperazinyl, morpholinyl, thiamorpholinyl, 4-methyl-piperazinyl, 4-phenyl-piperazinyl, 2,6-dimethyl-piperazinyl, 3,3-dimethylpiperidinyl and 2,6-dimethylmorpholinyl. A preferred group of compounds comprises those compounds of formula I wherein A represents the groups (a) or (b), R represents a $(C_{1-4})$alkyl radical, $R_1$ is methyl, $R_2$ is selected from $(C_{1-4})$alkyl, hydroxy$(C_{2-4})$alkyl, $(C_{2-4})$alkanoylmethyl, carbo$(C_{1-3})$-alkoxymethyl, the group

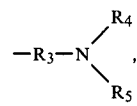

wherein $R_3$ represents an alkylene from 2 to 4 carbon atoms and $R_4$ and $R_5$ together with the nitrogein atom are piperazino or 4-phenylpiperazino, or $R_2$ represent nil, the dotted lines x and y represent nil or additional bonds; with the proviso that, when the symbol $R_2$ linked to the oxygen atom is different from nil, x is an additional bond and y and the other symbol $R_2$ represent nil; with the further proviso that, when the symbol $R_2$ linked to the nitrogen atom is different from nil, y is an additional bond and x and the other symbol $R_2$ represent nil; and salts therewith of pharmaceutically acceptable acids.

A most preferred group of compounds comprises those compounds of formula I wherein A represents the group (a), R is a $(C_{1-4})$alkyl radical and $R_1$ is methyl, $R_2$ is selected from $(C_{1-4})$alkyl, hydroxy $(C_{2-4})$alkyl, $(C_{2-4})$alkanoylmethyl, the group

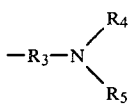

wherein $R_3$ is an alkylene from 2 to 4 carbon atoms and $R_4$ and $R_5$ together with the nitrogen atom are piperazino or 4-phenylpiperazino, or $R_2$ represent nil, the dotted lines x and y represent nil or additional bonds; with the proviso that, when the symbol $R_2$ linked to the oxygen atom is different from nil, x is an additional bond and y and the other symbol $R_2$ represent nil; with the further proviso that, when the symbol $R_2$ linked to the nitrogen atom is different from nil, y is an additional bond and x and the other symbol $R_2$ represent nil; and salts therewith of pharmaceutically acceptable acids. Another most preferred group of compounds comprises those compounds of formula I wherein A is the group (b), R is a $(C_{1-4})$alkyl radical, $R_2$ is selected from $(C_{1-4})$alkyl, hydroxy $(C_{2-4})$alkyl, carbo$(C_{1-3})$alkoxymethyl, the group

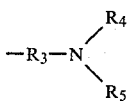

wherein $R_3$ is an alkylene from 2 to 4 carbon atoms and $R_4$ and $R_5$ together with the nitrogen atom are piperazino or 4-phenylpiperazino, or $R_2$ represent nil, the dotted lines x and y represent nil or additional bonds; with the proviso that, when the symbol $R_2$ linked to the oxygen atom is different from nil, x is an additional bond and y and the other symbol $R_2$ represent nil; with the further proviso that, when the symbol $R_2$ linked to the nitrogen atom is different from nil, y is an additional bond and x and the other symbol $R_2$ represent nil; and salts therewith of pharmaceutically acceptable acids.

The general method for preparing the compounds of the invention is an alkylation reaction wherein a compound of formula

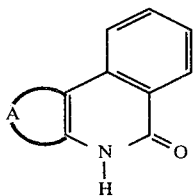

II or the corresponding enolic form, is reacted with a halide of formula

$R_2$-hal                III

In the compounds of formulas II and III the symbol A is defined as above, $R_2$ is defined as above but is different from nil and hal represents a halogen atom selected from chlorine, bromine and iodine and, preferably, bromine and iodine. When compounds of formula I are desired in which one of the two radicals $R_2$ is a $(C_{1-4})$alkyl group, also $(C_{1-4})$alkylsulfates may be advantageously employed. The process is carried out by dissolving or suspending a molar amount of the selected compound of formula II in an inert organic solvent, such as, for instance, dioxane, tetrahydrofurane or, preferably, dimethylformamide, and adding to the obtained solution or suspension an amount of a strong alkali agent corresponding to an equivalent molar amount or even a slight molar excess over the compound of formula II. Suitable alkali agents may be selected from alkali alkoxides such as, for instance, sodium methoxide, sodium ethoxide or potassium tert-butoxide, alkali metals and, preferably, alkali hydrides, e.g. sodium or potassium hydride. The obtained reaction mixture is kept for 2–3 hours at a temperature comprised between about 50° and about 70° C., preferably at about 60° C., then, after cooling to room temperature, a slight molar excess of the compound of formula III is added and the obtained mixture is heated for about 1–2 hours at a temperature comprised between about 50° and about 70° C., preferably at about 60° C. The mixture is finally worked up according to conventional techniques. Pursuant to this procedure, mixtures in various yields of the end compounds of formula I wherein the substituent $R_2$ is linked either to the nitrogen atom or to the oxygen atom may be obtained in different percentages. The percentage of an isomer with respect to the other one essentially depends on the nature of the nucleus A and, although a general rule cannot be established, it has been found that, when A represents the moiety (a), the O-substituted compounds (hereinafter referred to as O-isomers) i.e., those compounds of formula I wherein the $R_2$ group on the nitrogen atom and y represent nil, x is an additional bond and the $R_2$ group on the oxygen atom is different from nil, are mainly obtained whereas, when A represents the moiety (b), the reaction affords mixtures of O-substituted and N-substituted compounds (hereinafter referred to as N-isomers), wherein the N-substituted compounds are those of formula I in which the $R_2$ group at the oxigen atom and x represents nil, y is an additional bond and the $R_2$ group on the nitrogen atom is different from nil. In any case, when a mixture of N-substituted and O-substituted compounds is obtained the single products may be isolated by means of common separation techniques, as an example by column chromatography or fractional crystallization.

Some of the compounds of the invention can advantageously be prepared by other routes which involve the transformation of a preexisting radical $R_2$ into another one falling within the scope of the invention. As an example, the compounds of formula I wherein one of the radicals $R_2$ is halo$(C_{2-4})$alkyl and the other one is nil, and x and y assume the pertinent meanings, are useful starting materials for preparing corresponding compounds of formula I wherein $R_2$ represents the group

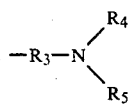

in which $R_3$, $R_4$ and $R_5$ are defined as above. These compounds are prepared simply by reacting the selected halo($C_{2-4}$)alkyl derivative with an amine of formula

according to known procedures.

In turn, it has been found that the compounds of formula I wherein one of the radicals $R_2$ is halo($C_{2-4}$)alkyl and the other one is nil, and x and y assume the pertinent meanings, may be conveniently prepared from the corresponding hydroxy($C_{2-4}$)alkyl derivatives by reaction with appropriate halogenating agents, as an example thionyl or phosphoryl halides or phosphorus pentahalides.

It has been observed, however, that, when this halogenation reaction is carried out on a substrate of formula

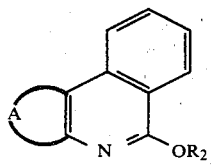

wherein A is defined as above and $R_2$ is a 2-hydroxyethyl or a 3-hydroxypropyl radical e.g., compounds of formula I wherein the $R_2$ radical on the nitrogen atom and y represent nil, x is an additional bond and the other $R_2$ is 2-hydroxyethyl or 3-hydroxypropyl, the reaction does not always afford the corresponding halo derivative, but a rearrangement may occur and compounds of formula V can be obtained in good yields

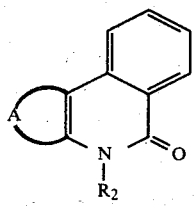

wherein A is defined as above and $R_2$ represents a 2-haloethyl or a 3-halopropyl group, in which halo stands for a halogen atom. The reaction is advantageously performed by dissolving or suspending a suitable amount of the compound of formula IV in an organic solvent such as, for instance, a ($C_{1-4}$) halogenated hydrocarbon and adding to the obtained solution or suspension a molar excess of the halogenating agent, preferably from about 1 to about 3 molar equivalents over the starting compound of formula IV. Although all of the common halogenating agents proved to act satisfactorily, it has been found that the best results are obtained by employing thionyl halides, e.g. thionyl chloride or thionyl bromide. The reaction is carried out at a temperature varying from about room temperature to about 70° C. and is completely within about 1-4 hours.

This type of rearrangement provides therefore a convenient route for preparing compounds of formula

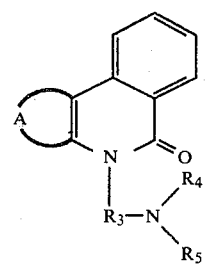

wherein A, $R_4$ and $R_5$ are defined as above and $R_3$ represents an alkylene of 2 or 3 carbon atoms which, obviously, fall within the scope embraced by the general formula I. They are prepared according to the usual method employed for alkylating amines with haloalkyl derivatives.

Finally, it will be clear to any person skilled in the art that other obvious routes for transforming a preexisting radical $R_2$ into another radical $R_2$ are intended to fall within the scope of the invention. When according to the above outlined processes, compounds of formula I are obtained as the corresponding salts of pharmaceutically acceptable acids, they may be converted into other pharmaceutically acceptable salts by reaction with a suitable acid or into the corresponding free base by treatment with an alkali agent. The free bases may in turn be transferred into the corresponding salts by reaction with predetermined pharmaceutically acceptable acids.

As stated above, the compounds of the invention possess CNS-depressant, anti-anxiety and antiinflammatory utility. Moreover, they display a considerably low toxicity as, generally, their $LD_{50}$ values are never lower than 600 mg/Kg when given i.p. and never lower than 1000 mg/Kg when given orally to mice.

The CNS-depressant activity in mammals was investigated by means of the general psychophysic screening method, as described by S. Irwin in Psychopharmacologia (Berl.), 13, 222–257, 1968. In particular, some representative experiments carried out on mice have shown that amounts from about 5 to about 100 mg/Kg i.p. of the compounds of Examples 4 (O-isomer), 7 (N-isomer), 8, 9, 10, 14, 18 (O-isomer), 23 and 42, were effective in inhibiting the spontaneous activity and the muscular tone, whereas amounts from about 30 to about 300 mg/Kg i.p. of the same compounds significantly impaired the motor coordinating and the righting reflex of the laboratory animals. It is to be noted that the above parameters are directly connected with sedative, hypnotic and miorelaxing properties. The antianxiety activity of the compounds of the invention was investigated by means of the "pole climbing avoidance test", performed as described by G. Maffii in Journ. Pharm. Pharmacol., 11, 129, 1959, wherein a conditioned animal (generally a rat) is deconditioned i.e., is brought to its normal psychic behavior by administration of a suitable amount of the compound to be tested. According to G. Maffii, an inhibition of the secondary conditioned response ($CR_2$) without a contemporary or coupled with a not significant inhibition of the primary conditioned response (CR) and the unconditioned response (UR) is a clear indication of an antianxiety effect since these last two parameters are connected with sedative and hypnotic properties.

Representative experiments carried out on groups of ten rats have shown that dosages varying from about 15 to about 60 mg/Kg of body weight administered i.p. of the compounds of Example 2(N-isomer), 5, 20, 24, 25, 26 and 38 are highly effective in inhibiting the $CR_2$- parameter and, contemporaneously, have practically no influence on the CR and the UR. The obtained results are summarized in the following table.

TABLE 1

| Compound of Example | $LD_{50}$ mg/Kg i.p. mice | Dose mg/Kg i.p. rats | $CR_2$ | CR | UR |
|---|---|---|---|---|---|
|  |  |  | Decond./ Conditioned | | |
| 2(Nisomer) | 400 | 30 | 8/10 | 0/10 | 0/10 |
|  |  | 15 | 5/10 | 0/10 | 0/10 |
| 5(N-isomer) | 600 | 60 | 5/10 | 0/10 | 0/10 |
| 5(O-isomer) | 600 | 60 | 5/10 | 0/10 | 0/10 |
| 20 | >600 | 60 | 9/10 | 3/10 | 0/10 |
|  |  | 30 | 7/10 | 3/10 | 0/10 |
|  |  | 10 | 6/10 | 1/10 | 0/10 |
| 24 | >600 | 60 | 10/10 | 3/10 | 0/10 |
|  |  | 30 | 6/10 | 0/10 | 0/10 |
| 25 | >600 | 60 | 7/10 | 0/10 | 0/10 |
|  |  | 30 | 5/10 | 0/10 | 0/10 |
| 26 | >600 | 60 | 10/10 | 0/10 | 0/10 |
|  |  | 30 | 5/10 | 0/10 | 0/10 |
| 38 | >600 | 60 | 10/10 | 4/10 | 0/10 |
|  |  | 30 | 9/10 | 1/10 | 0/10 |

> = higher than

As stated above, the compounds of the invention show also a remarkable antiinflammatory action, which was ascertained by means of the "carrageenin induced edema test" in rats. Said test was performed according to the operative scheme proposed by C. A. Winter et al., Proc., Soc. Exptl. Biol. Med. 111, 544, 1962 and it was found that oral dosages comprised between about 1/5 and about 1/10 of the $LD_{50}$ values of the compounds of Example 1, 5(N-isomer), 9, 24 and 26 are able to cause a significant reduction of the edema of 40% or more over the control.

The obtained results are summarized in the following table.

TABLE 2

| Compound of Example | $LD_{50}$ mg/kg p.o. mice | Dose mg/kg p.o. rats | % Decrease of the induced edema |
|---|---|---|---|
| 1 | >1000 | 20 | 25 |
|  |  | 50 | 38 |
|  |  | 100 | 46 |
|  |  | 200 | 61 |
| 5(N-isomer) | >1000 | 50 | 28 |
|  |  | 100 | 37 |
|  |  | 200 | 51 |
| 9 | 1000 | 50 | 25 |
|  |  | 100 | 31 |
|  |  | 200 | 40 |
| 24 | 1000 | 50 | 26 |
|  |  | 100 | 38 |
|  |  | 200 | 45 |
| 26 | >1000 | 50 | 30 |
|  |  | 100 | 37 |
|  |  | 200 | 43 |

The compounds of the invention may be administered by different routes. While the preferred routes of administration are oral and rectal, parenteral administration can also be employed.

For oral administration, the compounds are compounded into pharmaceutical dosages forms, such as, for instance, tablets, capsules, elixirs, solutions and the like. The dosage unit may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives.

The dosage range is from about 0.05 to about 2.00 g per day, preferably administered in divided dose.

Accordingly the present invention provides a therapeutic composition comprising as the active ingredient an amount of the compound of the invention from about 25 to about 250 mg together with a pharmaceutically acceptable carrier. The following additional description and examples further describe the invention and the manner and process of making and using it to enable the art skilled to make and use the same and set forth the best mode contemplated by the inventors of carrying out the invention.

EXAMPLE 1

2,4-Dimethyl-thiazolo[5,4-c]isoquinoline-5(4H)-one (N-isomer)

A suspension of 6.48 g. (0.030 mole) of 2-methyl-thiazolo[5,4-c]isoquinoline-5(4H)-one in 64 ml of dimethylformamide was added with 1.45 g of a 50% (by weight) suspension of sodium hydride in mineral oil (0.030 mole of sodium hydride). The resulting mixture was kept at 60° C. for 2 hours and, after cooling to room temperature, was added with 2.37 ml (0.038 mole) of methyl iodide and heated for 1 hour at 60° C. After evaporating the solvent, the residue was taken up with water and the obtained solid was collected, washed with water, dried and finally crystallized from methylene chloride/methanol. Yield 4.5 (65%) of the title compound. M.p. 174–176. The compound is the N-isomer.

The O-isomer was not obtained.

EXAMPLES 2–26

The following compounds were prepared according to the procedure of Example 1, starting from the appropriate compounds of formulas II and III. When mixtures of the N- and O- isomers were obtained, the single compounds were isolated by column chromatography or fractioned crystallization. The yields were calculated over the starting compound of formula II.

EXAMPLE 2

4-Ethyl-2-methyl-thiazolo[5,4-c]isoquinoline-5(4H)-one (N-isomer) and 5-ethoxy-2-methyl-thiazolo[5,4-c]isoquinoline (O-isomer), from 2-methyl-thiazolo[5,4-c]-5(4H)-one and ethyl iodide. N-isomer: yield 46%, m.p. 152°–54° C. O-isomer: yield 10%: m.p. 103°–05° C.

EXAMPLE 3

2-Methyl-4-propyl-thiazolo[5,4-c]isoquinoline-5(4H)-one (N-isomer) and 2-methyl-5-propoxy-thiazolo[5,4-c]isoquinoline (O-isomer), from 2-methyl-thiazolo[5,4-c]isoquinoline-5(4H)-one and propyl iodide. N-isomer: yield 52%, m.p. 123°–25° C. O-isomer: yield 13%, m.p. 68°–69° C.

EXAMPLE 4

4-Isopropyl-2-methyl-thiazolo[5,4-c]isoquinoline-5(4H)-one (N-isomer) and 5-isopropoxy-2-methyl-thiazolo[5,4-c]isoquinoline (O-isomer), from 2-methyl-thiazolo[5,4-c]isoquinoline-5(4H)-one and isopropyl iodide. N-isomer: yield 12%, m.p. 90°-91° C. O-isomer: yield 44%, m.p. 109°-10° C.

EXAMPLE 5

4-Butyl-2-methyl-thiazolo[5,4-c]isoquinoline-5(4H)-one (N-isomer) and 5-butoxy-2-methyl-thiazolo[5,4-c]isoquinoline (O-isomer), from 2-methyl-thiazolo[5,4-c]isoquinoline-5(4H)-one and butyl bromide. N-isomer: yield 52%, m.p. 123°-25° C. O-isomer: yield 19%, m.p. 93°-95° C.

EXAMPLE 6

4-[2-(Diethylamino)ethyl]-2-methyl-thiazolo[5,4-c]isoquinoline-5(4H)-one (N-isomer) and 5-[2-(diethylamino)ethoxy]-2-methyl-thiazolo[5,4-c]isoquinoline (O-isomer), from 2-methyl-thiazolo[5,4-c[isoquinoline-5(4H)-one and 1-diethylamino-2-chloroethane hydrochloride. N-isomer (as the hydrochloride): yield 43%, m.p. 235°-38° C. O-isomer (as the hydrochloride): 10%, m.p. 218°-21° C.

EXAMPLE 7

4-Carbethoxymethyl-2-methyl-thiazolo[5,4-c]isoquinoline-5(4H)-one (N-isomer) and 5-carbethoxymethoxy-2-methyl-thiazolo[5,4-c]isoquinoline (O-isomer), from 2-methyl-thiazolo[5,4-c]isoquinoline-5(4H)-one and the ethyl ester of α-bromo-acetic acid. N-isomer: yield 58%, m.p. 161°-63° C. O-isomer: yield 8%, m.p. 99°-101° C.

EXAMPLE 8

4-(2-Hydroxyethyl)-2-methyl-thiazolo[5,4-c]isoquinoline-5(4H)-one (N-isomer), from 2-methyl-thiazolo[5,4-c]isoquinoline-5(4H)-one and 2-bromoethanol. Yield: 50%. M.p. 216°-19° C.

EXAMPLE 9

2-Ethyl-4-methyl-thiazolo[5,4-c]isoquinoline-5(4H)-one (N-isomer), from 2-ethyl-thiazolo[5,4-c]isoquinoline-5(4)-one and methyl iodide. Yield 77%, m.p. 175°-77° C.

EXAMPLE 10

2-Butyl-4-(2-hydroxyethyl)-thiazolo[5,4-c]isoquinoline-5(4H)-one N-isomer), from 2-butyl-thiazolo[5,4-c]isoquinoline-5(4H)-one and 2-bromoethanol, Yield 64%, m.p. 98°-99° C.

EXAMPLE 11

2-Butyl-4-methyl-thiazolo[5,4-c]isoquinoline-5(4H)-one (N-isomer), from 2-butyl-thiazolo[5,4-c]isoquinoline-5(4H)-one and methyl iodide. Yield 79%, m.p. 91°-93° C.

EXAMPLE 12

4-Methyl-2-phenyl-thiazolo[5,4-c]isoquinoline-5(4H)-one (N-isomer), from 2-phenyl-thiazolo[5,4-c]isoquinoline-5(4H)-one and methyl iodide. Yield 77%, m.p. 175°-77° C.

EXAMPLE 13

4-(2-Hydroxyethyl)-2-phenyl-thiazolo[5,4-c]isoquinoline-5(4H)-one (N-isomer), from 2-phenyl-thiazolo[5,4-c]isoquinoline-5(4H)-one and 2-bromoethanol. Yield 61%, m.p. 195°-98° C.

EXAMPLE 14

1-Methyl-3-phenyl-5(2-hydroxyethoxy)-3H-pyrazolo[3,4-c]isoquinoline (O-isomer), from 1-methyl-3-phenyl-3H-pyrazolo[3,4-c]isoquinoline-5(4H)-one and 2-bromoethanol. Yield 86%, m.p. 177°-80° C.

EXAMPLE 15

5-[2-(Diethylamino)ethoxy]-1-methyl-3-phenyl-3H-pyrazolo[3,4-c]isoquinoline hydrochloride (O-isomer) from 1-methyl-3-phenyl-3H-pyrazolo[3,4-c]isoquinoline-5(4H)-one and 1-diethylamino-2-chloro-ethane hydrochloride. Yield 50%, m.p. 224°-27° C.

EXAMPLE 16

5-(2-Hydroxyethoxy)-3-phenyl-3H-pyrazolo[3,4-c]isoquinoline (O-isomer) from 3-phenyl-3H-pyrazolo[3,4-c]isoquinoline-5(4H)-one and 2-bromoethanol. Yield 70%, m.p. 172°-75° C.

EXAMPLE 17

5-[2-(Diethylamino)ethoxy]-3-phenyl-3H-pyrazolo[3,4-c]isoquinoline (O-isomer) hydrochloride from 3-phenyl-3H-pyrazolo[3,4-c]isoquinoline-5(4H)-one and 1-diethylamino-2-chloro-ethane hydrochloride. Yielad 71%, m.p. 226°-28° C.

EXAMPLE 18

1,3,4-Trimethyl-3H-pyrazolo[3,4-c]isoquinoline-5(4H)-one (N-isomer) and 1,3-dimethyl-5-methoxy-3H-pyrazolo[3,4-c]isoquinoline (O-isomer), from 1,3-dimethyl-3H-pyrazolo[3,4-c]isoquinoline-5(4H)-one and methyl iodide. N-isomer: yield 48%, m.p. 186°-89° C. O-isomer: yield 38%, m.p. 94°-97° C.

EXAMPLE 19

4-Acetylmethyl-1,3-dimethyl-3H-pyrazolo[3,4-c]isoquinoline-5(4H)-one (N-isomer and 5-acetylmethoxy-1,3-dimethyl-3H-pyrazolo[3,4-c]isoquinoline, (O-isomer) from 1,3-dimethyl-3H-pyrazolo[3,4-c]isoquinoline-5(4H)-one and bromoacetone. N-isomer: yield 14%, m.p. 215°-18° C. O-isomer: yield 43%, m.p. 152°-55° C.

EXAMPLE 20

5-(2-Hydroxyethoxy)-1,3-dimethyl-3H-pyrazolo[3,4-c]isoquinoline (O-isomer), from 1,3-dimethyl-3H-pyrazolo[3,4-c]isoquinoline-5(4H)-one and 2-bromoethanol. Yield 49%, m.p. 135°-38° C.

EXAMPLE 21

5-Carbethoxymethoxy-1,3-dimethyl-3H-pyrazolo[3,4-c]isoquinoline (O-isomer), from 1,3-dimethyl-3H-pyrazolo[3,4-c]isoquinoline-5(4H)-one and α-bromo-acetic acid ethyl ester. Yield 71%, m.p. 97°-100° C.

EXAMPLE 22

5-Ethoxy-1,3-dimethyl-3H-pyrazolo[3,4-c]isoquinoline (O-isomer), from 1,3-dimethyl-3H-pyrazolo[3,4-c]isoquinoline-5(4H)-one and ethyl bromide. Yield 61%, m.p. 89° C.

EXAMPLE 23

1,3-Dimethyl-5-propoxy-3H-pyrazolo[3,4-c]isoquinoline (O-isomer), from 1,3-dimethyl-3H-pyrazolo[3,4-c]isoquinoline-5(4H)-one and propyl bromide. Yield 75%, m.p. 78°–80° C.

EXAMPLE 24

5-Butoxy-1,3-dimethyl-3H-pyrazolo[3,4-c]isoquinoline (O-isomer), from 1,3-dimethyl-3H-pyrazolo[3,4-c]isoquinoline-5(4H)-one and butyl bromide. Yield 64%, m.p. 60°–63° C.

EXAMPLE 25

1-Ethyl-5-hydroxyethoxy-3-methyl-3H-pyrazolo[3,4-c]isoquinoline (O-isomer), from 1-ethyl-3-methyl-3H-pyrazolo[3,4-c]isoquinoline-5(4H)-one and 2-bromoethanol. Yield 53%, m.p. 165°–68° C.

EXAMPLE 26

5-Acetylmethoxy-1-ethyl-3-methyl-3H-pyrazolo[3,4-c]isoquinoline (O-isomer), from 1-ethyl-3-methyl-3H-pyrazolo[3,4-c]isoquinoline-5(4H)-one and bromoacetone. Yield 31%, m.p. 105°–8° C.

EXAMPLE 27

4-(2-Chloroethyl)-3-phenyl-3H-pyrazolo[3,4-c]isoquinoline-5(4H)-one.

A solution of 10.0 g. (0.0328 mole) of the compound of Example 16 dissolved in 200 ml of methylene chloride was added with 4.75 ml (0.0655 mole) of thionyl chloride dissolved in 30 ml of methylene chloride and the resulting mixture was heated at about 45° C. for 3 hours. After cooling, 400 ml of an aqueous saturated solution of sodium carbonate was added to the reaction mixture, the organic phase was separated and the organic solvent was evaporated in vacuo. The obtained solid residue was crystallized from ethanol. Yield 9 g. (84%). M.p. 157°–60° C.

EXAMPLE 28–30

The following compounds were prepared as described in Example 27, starting from the appropriate 5-hydroxyalkoxy or 4-hydroxyalkyl derivative. The yields were calculated over the corresponding hydroxyalkoxy or hydroxyalkyl compound.

EXAMPLE 28

4-(2-Chloroethyl)-1,3-dimethyl-3H-pyrazolo[3,4-c]isoquinoline-5(4H)-one, from the compound of Example 20 and thionyl chloride. Yield 87%, m.p. 153°–53° C.

EXAMPLE 29

4-(Chloroethyl)-1-methyl-3-phenyl-3H-pyrazolo[3,4-c]isoquinoline-5(4H), one, from the compound of Example 14 and thionyl chloride Yield 84%, m.p. 188°–90° C.

EXAMPLE 30

2-Butyl-4-(2-chloroethyl)-thiazolo[5,4-c]isoquinoline-5(4H)-one from the compound of Example 10 and thionyl chloride. Yield 93%, m.p. 125°–26° C.

EXAMPLE 31

4-[2-(Diethylamino)ethyl]-3-phenyl-3H-pyrazolo[3,4-c]isoquinoline-5(4H)-one hydrochloride.

Four grams (0.0123 mole) of the compound of Example 27, 3.81 ml (0.0369 mole) of diethylamine and 80 ml of dimethylformamide were heated at 80° C. for 6 hours. After evaporating the solvent, the reaction mass was taken up with chloroform, and the obtained organic solution was first washed with a saturated aqueous solution of sodium carbonate and then with water (twice). After drying over sodium sulfate, the chloroform was evaporated off and the obtained residue was passed through a silica-gel column by eluting with chloroform-:methanol=99:1 (by volume). The obtained product was finally dissolved in diethyl ether and treated with a saturated solution of hydrogen chloride in diethyl ether whereby the title compound crystallized out. Yield 3.7 g. (76%). M.p. 252°–56° C.

EXAMPLES 32–42

The following compounds were prepared according to the same procedure outlined in the foregoing Example, starting from the appropriate 4-haloalkyl derivative. The yields were calculated over the corresponding hydroxyalkyl compound.

EXAMPLE 32

3-Phenyl-4-[2-(4-phenyl-1-piperazinyl)ethyl]-3H-pyrazolo[3,4-c]isoquinoline-5(4H)-one, from the compound of Example 27 and 4-phenyl-piperazine. Yield 68%, m.p. 139°–41° C.

EXAMPLE 33

4-[2-(Diethylamino)ethyl]-1-methyl-3-phenyl-3H-pyrazolo[3,4-c]isoquinoline-5(4H)-one, from the compound of Example 29 and diethylamine. Yield 68%, m.p. 113°–15° C.

EXAMPLE 34

1-Methyl-3-phenyl-4-[2-(4-phenyl-1-piperazinyl)ethyl]-3H-pyrazolo[3,4-c]isoquinoline-5(4H)-one, from the compound of Example 29 and 4-phenyl-piperazine. Yield 51%, m.p. 164°–65° C.

EXAMPLE 35

1,3-Dimethyl-4-[2-(dimethylamino)ethyl]-3H-pyrazolo[3,4-c]isoquinoline-5(4H)-one, from the compound of Example 28 and dimethylamine. Yield 75%, m.p. 103°–05° C.

EXAMPLE 36

4-[2-(Diethylamino)ethyl]-1,3-dimethyl-3H-pyrazolo[3,4-c]isoquinoline-5(4H)-one, from the compound of Example 28 and diethylamine. Yield 73%, m.p. 77°–79° C.

EXAMPLE 37

1,3-Dimethyl-4-[2-(1-piperidinyl)ethyl]-3H-pyrazolo[3,4-c]isoquinoline-5(4H)-one hydrochloride, from the compound of Example 28 and piperidine. Yield 46%, m.p. 262°–65° C.

EXAMPLE 38

1,3-Dimethyl-4-[2-(4-phenyl-1-piperazinyl)ethyl]-3H-pyrazolo[3,4-c]isoquinoline-5(4H)-one hydrochloride, from the compound of Example 28 and 4-phenyl-piperazine. Yield 74%, m.p. 263°–65° C.

EXAMPLE 39

4-Isopropylaminoethyl-1,3-dimethyl-3H-pyrazolo[3,4-c]isoquinoline-5(4H)-one hydrochloride, from the compound of Example 28 and isopropylamine. Yield 75%, m.p. 279°–81° C.

EXAMPLE 40

2-Butyl-4-[2-(1-piperidinyl)ethyl]-thiazolo[5,4-c]isoquinoline-5(4H)-one oxalate, from the compound of Example 30 and piperidine. Yirld 66%, 215°–18° C.

EXAMPLE 41

2-Butyl-4-[2-(butylamino)ethyl]-thiazolo[5,4-c]isoquinoline-5(4H)-one oxalate, from the compound of Example 30 and butylamine. Yield 60%, m.p. 224°–25° C.

EXAMPLE 42

2-Butyl-4-[2-(4-phenyl-1-piperazinyl)ethyl]-thiazolo[5,4-c]isoquinoline-5(4H)-one, from the compound of Example 30 and 4-phenyl-piperazine. Yield 50%, m.p. 81° C.

EXAMPLE 43

A tablet is prepared with
1,3-Dimethyl-4-[2-(4-phenyl-1-piperazinyl) ethyl]-3H-pyrazolo[3,4-c]isoquinoline-5(4H)-one hydrochloride: 150 mg
Saccharose: 30 mg
Polyvinylpyrrolidone: 5 mg
Sodium dioctylsulfosuccinate: 1.4 mg
Magnesium stearate: 8 mg
Corn starch: q.s. to 250 mg

EXAMPLE 44

A capsule is prepared with
1,3-Dimethyl-4-[2-(4-phenyl-1-piperazinyl) ethyl]-3H-pyrazolo[3,4-c]isoquinoline-5(4H)-one hydrochloride: 200 mg
Saccharose: 35 mg
Polyvinylpyrrolidone: 5 mg
Sodium dioctylsulfosuccinate: 1.8 mg
Magnesium stearate: 10 mg
Corn starch: q.s. to 300 mg

EXAMPLE 45

A sugar coated tablet is prepared with
2,4-dimethyl-thiazolo[5,4-c]isoquinoline-5(4H)-one: 50 mg
Polyvinylpyrrolidone: 2 mg
Sodium carboxymethylcellulose: 1.5 mg
Avicel ®: 5 mg
Titanium dioxide: 2 mg
Magnesium stearate: 2.5 mg
Corn starch: 8 mg
Gum arabic: 5 mg
Talc: 10 mg
Kaolin: 2 mg
Saccharose: q.s. to 150 mg Preparation of the starting materials of formula II 1,3-Dimethyl-3H-pyrazolo[3,4-c]isoquinoline-5(4H)-one To 42.6 g (0.228 mole) of 5-amino-1,3-dimethyl-4-phenyl-3H-pyrazole in 450 ml of benzene and 170 ml of anhydrous ethyl acetate, 30 g (0.252 mole) of phenylisocyanate was gradually added with stirring at room temperature. The reaction mixture was heated to 60° C. for 4 hours, cooled and the precipitate which formed was filtered under vacuum and washed with ethyl ether, giving 69 g of the corresponding phenylurea derivative. (m.p. 200°–204° C.).

10 Grams of this compound were melted at 280° C. for 10 minutes and the residue was crystallized from dimethylformamide, giving 6.2 g of the desired product. M.p. 310° C.; yield 89%.

The following compounds of formula II were prepared substantially as described in the foregoing example, starting from the corresponding 5-aminopyrazole or 5-aminothiazole and phenylisocyanate, and cyclizing the obtained phenylurea.

| Compound | M.p. °C. |
|---|---|
| 1-Methyl-3-phenyl-3H-pyrazolo[3,4-c]isoquinoline-5(4H)-one | 298–304 |
| 3-Phenyl-3H-pyrazolo[3,4-c]isoquinoline-5(4H)-one | 284–286 |
| 1-Ethyl-3-methyl-3H-pyrazolo[3,4-c]isoquinoline-5(4H)-one | 291–294 |
| 2-Methyl-thiazolo[5,4-c]isoquinoline-5(4H)-one | 310–320 |
| 2-Ethyl-thiazolo[5,4-c]isoquinoline-5(4H)-one | 254–257 |
| 2-Butyl-thiazolo[5,4-c]isoquinoline-5(4H)-one | 172–173 |
| 2-Phenyl-thiazolo[5,4-c]isoquinoline-5(4H)-one | >310 |
| 2-(p-Tolyl)-thiazolo[5,4-c]isoquinoline-5(4H)-one | >300 |

We claim:

1. A tricyclic orthofused heterocyclic compound of the formula

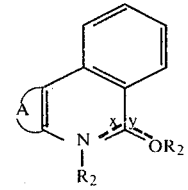

wherein A is the group

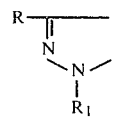

or the group

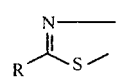

in which R represents hydrogen, $(C_{1-4})$alkyl, phenyl or tolyl and $R_1$ may be $(C_{1-4})$alkyl, phenyl or tolyl, $R_2$ is selected from $(C_{1-4})$alkyl, $(C_{2-4})$alkanoylmethyl, carbo-$(C_{1-3})$alkoxymethyl, hydroxy$(C_{2-4})$alkyl, halo$(C_{2-4})$alkyl and a group

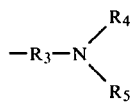

wherein R₃ is an alkylene group from 2 to 4 carbon atoms and R₄ and R₅ independently represent hydrogen or (C₁₋₄)alkyl or, taken together with the nitrogen atom, a fully hydrogenated 5- or 6-membered heterocyclic radical which may contain a further heteroatom selected from O, N and S wherein the heteroatoms are in 1, 4-positions when said heterocyclic radical is 6-membered and wherein the heterocyclic radicals may be optionally substituted by a (C₁₋₄)alkyl or phenyl group, or R₂ may represent nil, the dotted lines x and y may represent nil or additional bonds; with the proviso that, when the symbol R₂ linked to the oxygen atom is different from nil, x is an additional bond and y and the other symbol R₂ represent nil; with the further proviso that, when the symbol R₂ linked to the nitrogen atom is different from nil, y is an additional bond and x and the other symbol R₂ represent nil; or a salt therewith of a pharmaceutically acceptable acid.

2. A compound as defined in claim 1 wherein A represents one of the groups (a) or (b), R represents a (C₁₋₄)alkyl radical, R₁ represents methyl, R₂ is selected from (C₁₋₄)alkyl, hydroxy(C₂₋₄)alkyl, (C₂₋₄)alkanoylmethyl, carbo (C₁₋₃)alkoxymethyl and the group

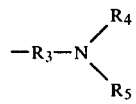

wherein R₃ represents an alkylene group of from 2 to 4 carbon atoms and R₄ and R₅ together with the nitrogen atom represent piperazino or 4-phenylpiperazino, or R₂ represents nil, the dotted lines x and y represent nil or additional bonds; with the proviso that, when the symbol R₂ linked to the oxygen atom is different from nil, x is an additional bond and y and the other symbol R₂ represent nil; with the further proviso that, when the symbol R₂ linked to the nitrogen atom is different from nil, y is an additional bond and x and the other symbol R₂ represent nil; or a salt therewith of a pharmaceutically acceptable acid.

3. A compound as defined in claim 1 wherein A represents the group (a), R represents a (C₁₋₄)alkyl radical and R₁ represents methyl, R₂ is selected from (C₁₋₄)alkyl, hydroxy (C₂₋₄)alkyl, (C₂₋₄)alkanoylmethyl and the group

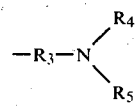

wherein R₃ is an alkylene group of from 2 to 4 carbon atoms and R₄ and R₅ together with the nitrogen atom represent piperazino or 4-phenylpiperazino, or R₂ represents nil, the dotted lines x and y represent nil or additional bonds; with the proviso that, when the symbol R₂ linked to the oxygen atom is different from nil, x is an additional bond and y and the other symbol R₂ represent nil; with the further proviso that, when the symbol R₂ linked to the nitrogen atom is different from nil, y is an additional bond and x and the other symbol R₂ represent nil; or a salt therewith of a pharmaceutically acceptable acid.

4. A compound as defined in claim 1, wherein A represents the group (b), R represents a (C₁₋₄)alkyl radical, R₂ is selected from (C₁₋₄)alkyl, hydroxy (C₂₋₄)alkyl, carbo (C₁₋₃)alkoxymethyl and the group

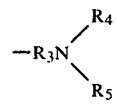

wherein R₃ is an alkylene group of from 2 to 4 carbon atoms and R₄ and R₅ together with the nitrogen atom represent piperazino or 4-phenylpiperazino, or R₂ represent nil, the dotted lines x and y represent nil or additional bonds; with the proviso that, when the symbol R₂ linked to the oxygen atom is different from nil, x is an additional bond and y and the other symbol R₂ represent nil; with the further proviso that, when the symbol R₂ linked to the nitrogen atom is different from nil, y is an additional bond and x and the other symbol R₂ represent nil; or a salt therewith of a pharmaceutically acceptable acid.

5. A compound as defined in claim 1, which is 2,4-dimethylthiazolo[5,4-c]isoquinoline-5(4H)-one.

6. A compound as defined in claim 1, which is 5-butoxy-1,3-dimethyl-3H-pyrazolo[3,4-c]isoquinoline.

7. A compound as defined in claim 1, which is 1,3-dimethyl-4-[2-(4-phenyl-1-piperazinyl)ethyl]-3H-pyrazolo[3,4-c]isoquinoline-5(4H)-one hydrochloride.

8. A pharmaceutical composition useful as a CNS-depressant and anti-inflammatory comprising from about 25 to about 250 mg of a compound of formula I as claimed in claim 1 as a salt therewith of a pharmaceutically acceptable acid in admixture with a pharmaceutically acceptable carrier.

9. A method for treating psychic disorders and inflammation in mammals, which comprises administering thereto a daily dosage of a compound of formula I as claimed in claim 1 or a salt therewith of a pharmaceutically acceptable acid in amount varying from about 0.05 to about 2.00 grams.

* * * * *